US011723356B2

(12) United States Patent
Seetharam (10) Patent No.: US 11,723,356 B2
(45) Date of Patent: Aug. 15, 2023

(54) MOSQUITO MANAGEMENT (71) Applicant: Brandenburg Innovation Limited, Brierley Hill (GB)

(72) Inventor: Shankar Seetharam, Brierley Hill (GB)

(73) Assignee: Brandenburg Innovation Limited

( * ) Notice: Subject to any disclaimer, the term of this patent is extended or adjusted under 35 U.S.C. 154(b) by 0 days.

(21) Appl. No.: 16/632,497

(22) PCT Filed: Jul. 23, 2018

(86) PCT No.: PCT/IB2018/000758
§ 371 (c)(1),
(2) Date: Jan. 20, 2020

(87) PCT Pub. No.: WO2019/016592
PCT Pub. Date: Jan. 24, 2019

(65) Prior Publication Data
US 2020/0221685 A1      Jul. 16, 2020

(30) Foreign Application Priority Data

Jul. 21, 2017    (GB) ..................................... 1711747

(51) Int. Cl.
*A01M 29/10* (2011.01)
*F21S 4/26* (2016.01)
*F21Y 115/10* (2016.01)

(52) U.S. Cl.
CPC ............... *A01M 29/10* (2013.01); *F21S 4/26* (2016.01); *F21Y 2115/10* (2016.08)

(58) Field of Classification Search
CPC ...... A01M 29/10; A01M 29/28; A01M 29/34; F21S 4/006; F21S 4/26; F21S 4/28; F21Y 2115/10

(Continued)

(56) References Cited

U.S. PATENT DOCUMENTS 10,260,735 B2 * 4/2019 Chien ................... F21V 33/004
2003/0190295 A1 * 10/2003 Fukui ..................... A61Q 19/10
424/59

(Continued)

FOREIGN PATENT DOCUMENTS

CN     102937271 A       2/2013
CN     204119431    *    1/2015

(Continued)

OTHER PUBLICATIONS

English abstract for CN-205155721.

(Continued)

*Primary Examiner* — Kerri L Mcnally
*Assistant Examiner* — Thang D Tran
(74) *Attorney, Agent, or Firm* — Fishman Stewart PLLC (57) ABSTRACT A method of repelling mosquitos from a locality or proximity where humans or animals will be present and/or inhibiting the mosquito from seeking a blood meal, may include positioning lighting at a location and in an orientation that will at least one of generate a photo-taxis repellent response and inhibit blood seeking by the mosquito, such that the mosquito at least one of (i) may be discouraged from entering a defined zone which the lighting protects, and (ii) may have a reduced tendency to seek a blood meal within the zone. The lighting may be LED lighting and may generate an intense light of at least 100 lux, with a colour temperature of greater than 5000K and may have a cool white spectra with two peaks, a first peak at about 450 nm-470 nm and a second peak at about 500 nm-700 nm.

15 Claims, 12 Drawing Sheets (58) Field of Classification Search
USPC .................................................. 340/573.2
See application file for complete search history.

(56) References Cited

U.S. PATENT DOCUMENTS

| | | | | |
|---|---|---|---|---|
| 2004/0246702 | A1* | 12/2004 | Yeh | H01J 9/20 362/84 |
| 2005/0036300 | A1* | 2/2005 | Dowling | A47G 19/2227 362/101 |
| 2005/0207152 | A1* | 9/2005 | Maxik | F21K 9/232 362/240 |
| 2007/0008080 | A1* | 1/2007 | Yen | A01M 29/16 340/384.2 |
| 2007/0086199 | A1* | 4/2007 | Demarest | H05B 45/20 362/441 |
| 2008/0001551 | A1* | 1/2008 | Abbondanzio | H05B 47/19 315/291 |
| 2008/0181352 | A1* | 7/2008 | Hirafuji | A01M 1/223 377/16 |
| 2008/0203899 | A1* | 8/2008 | Miller | H01J 1/74 313/499 |
| 2008/0259589 | A1* | 10/2008 | Van De Ven | F21K 9/00 362/231 |
| 2012/0032096 | A1* | 2/2012 | Marka | A01M 29/10 250/492.1 |
| 2012/0210637 | A1* | 8/2012 | Kamahara | A01G 22/05 47/17 |
| 2013/0241391 | A1* | 9/2013 | Takei | H01L 25/0753 313/112 |
| 2014/0126137 | A1* | 5/2014 | Leonard | D02G 3/448 361/679.31 |
| 2014/0362560 | A1* | 12/2014 | Formico | F21V 15/01 239/302 |
| 2015/0144713 | A1* | 5/2015 | Formico | A01M 29/12 239/276 |
| 2015/0223411 | A1* | 8/2015 | Toye | A01G 13/0268 442/49 |
| 2016/0003431 | A1* | 1/2016 | Chien | F21V 5/04 362/641 |
| 2016/0025283 | A1* | 1/2016 | Chen | F21V 21/145 362/190 |
| 2016/0029643 | A1* | 2/2016 | Iatrou | A01N 35/04 424/725 |
| 2016/0061396 | A1* | 3/2016 | Bosua | F21K 9/238 362/231 |
| 2016/0262313 | A1* | 9/2016 | Szeto | A01M 29/10 |
| 2016/0273154 | A1* | 9/2016 | France | D06H 3/08 |
| 2017/0071184 | A1* | 3/2017 | Zheng | A01M 1/223 |
| 2017/0086391 | A1* | 3/2017 | Vilgiate | H05B 47/19 |
| 2017/0216164 | A1* | 8/2017 | Traynor | A61K 8/731 |
| 2017/0233324 | A1* | 8/2017 | Reddy | C07C 49/643 568/373 |
| 2017/0295783 | A1* | 10/2017 | Li | A01N 65/44 |
| 2017/0299148 | A1* | 10/2017 | Xie | F21S 2/00 |
| 2018/0043130 | A1* | 2/2018 | Moore-Ede | H05B 47/105 |
| 2018/0116196 | A1* | 5/2018 | Van Kleef | A01M 29/12 |
| 2018/0317479 | A1* | 11/2018 | Doyle | A01N 33/26 |

FOREIGN PATENT DOCUMENTS

| | | | |
|---|---|---|---|
| CN | 205155606 U | | 4/2016 |
| CN | 205155721 | * | 4/2016 |
| CN | 205155721 U | | 4/2016 |
| CN | 207707146 | * | 8/2018 |
| EP | 1462711 A1 | | 9/2004 |
| JP | 2012243744 A | | 12/2012 |
| WO | 2016068368 | | 10/2014 |
| WO | 2016096367 | | 6/2016 |
| WO | WO 2016096367 | * | 6/2016 |
| WO | 2017085682 | | 5/2017 |
| WO | WO 2017085682 | * | 5/2017 |

OTHER PUBLICATIONS

English abstract for JP-2012243744.
English abstract for CN-2005155606.
English abstract for CN-102937271.

* cited by examiner

MOSQUITO MANAGEMENT

CROSS-REFERENCE TO RELATED APPLICATIONS

This application claims priority to International Patent Application No. PCT/IB2018/000758, filed on Jul. 23, 2018 and British Patent Application No. GB 1711747.4. filed on Jul. 21, 2017, the contents of both of which are hereby incorporated herewith in their entireties.

TECHNICAL FIELD

This invention relates to the management of mosquitos, and more particularly to the use of light, not as an attractant but as a repellent (i.e. to elicit a negative photo-taxis response) and I or to inhibit blood seeking activity.

Preferably the light is an intense light.

Brightness B is measured in lux (lumens/m$^2$) which can be equated to light intensity.

By "intense" is meant the light generated has a brightness of at least 5 lux, more preferably at least 100 lux, and more preferably still at least 200 lux (which is the lux measured at a distance of 1 m). More preferably it has a brightness of between 270 lux and 310 lux, optimally about 290 lux. Above 310 lux no additional negative photo-taxis response is observed.

Preferably the light has a colour temperature of greater than 5000K, and is most preferably in the range 5000K-10000K.

Preferably the light has a "cool white" spectra, i.e. one exhibiting two peaks—a first peak at about 450 nm-470 nm (the peak with a greater amplitude) and a second peak at about 500 nm-700 nm (a broader peak of lesser amplitude than the first peak).

Preferably, but not essentially, the light source is a light emitting diode, hereafter LED. The LED may be a single LED or comprise an array of LED's, particularly strips comprising linearly spaced LED's in lengths ranging from 10's of centimetres to several metres in length depending on the application. In other embodiments the light source can take other forms allowing the light to be directed with a narrow spread (less than 90°), an intermediate spread (90° to 180°) or a broad spread (between 180° and 360°). The light can also be positioned to be directional e.g. up or down or from the side depending on the application.

Preferably, the light is positioned to direct the light in a direction optimal for its purpose, which may be, for example, to prevent mosquitos entering a building through openings, such as, doors and windows, a tent through its opening, or an environment in which humans sit, such as a patio area or alfresco dining area. In such circumstances it may be desirable to partially or substantially encircle the area and orientate the lights so the light is projected into the seated area. Again, the light might be projected from above, below and/or from one or more sides.

By repelling the mosquitos from a human or animal host and/or inhibiting blood seeking activity, it may be possible to reduce the incidence of mosquitos biting hosts and in consequence reduce mosquito borne disease transmission.

BACKGROUND

Mosquito borne diseases cause the most number of human fatalities yearly throughout the world, and have killed more humans than all the world wars put together. With over 2700 species of mosquitoes known globally, mosquitoes have adapted and evolved to fill many tropical and sub-tropical niches around the world. With onset of global warming this global distribution is increasing everyday as mosquitoes find new niches to adapt and invade. They are vectors of diseases, which mean they carry diseases from one animal to another without being affected by the disease themselves. This vector disease transmission in mosquitoes is usually transmitted by the female mosquito, as they possess the necessary mouth parts to pierce the epidermis of animals to draw out a blood meal. It is from this blood meal that female mosquitoes derive the essential amino acids for egg production and hence reproduction.

The two most notorious species of mosquito are *Aedes aegypti* and *Aedes albopictus*. Native to Africa and Asia respectively, their distribution globally has been significantly increased due to the movement of people, and goods, around the world. In many tropical countries, these two species of mosquitoes share the same environmental niche and in turn cause twice the disease transmission.

They are both known vectors of Dengue Fever and Dengue Haemorrhagic Fever, which account for greater than 90 million clinically reported infections of Dengue per year in over 100 countries. Of these 90 million cases yearly more than 500,000 manifests to the more virulent form of Dengue known as Dengue Haemorrhagic Fever, which has a higher chance of human mortality than just Dengue alone. Every year Dengue causes more than 25,000 deaths.

However, with modern research and diagnostics, new emerging diseases transmitted by these mosquitoes have been identified. These include Chikungunya, 30 Mayaro, Usutu and Zika. In 2015-2017, Zika, has been reported in 70 different countries with over 1 million cases in the Americas alone.

Female *Aedes* mosquitoes preferred times for seeking a blood meal are at dawn and dusk, but biting can occur throughout the day if conditions are favourable (temperature/humidity dependent). The mosquito becomes infective approximately seven days after it has bitten a person or animal carrying these viruses. This is the extrinsic incubation period, during which time the virus replicates in the mosquito and reaches the salivary glands. The average lifespan of an *Aedes* mosquito in nature is two weeks. Female mosquitoes will lay eggs about three times in her lifetime, and about 100 eggs are produced each time. If she is infective, she can also transfer the virus to her eggs, this is known as Transovarian transmission, and is a common precursor to the start of many outbreaks. The eggs can lie dormant in dry conditions for up to about nine months, after which they can hatch if exposed to favourable conditions, i.e. water and food.

The most common methods used to control these mosquitoes are by Adulticiding and Larviciding. Adulticiding is the administering of insecticide through aerial spraying, or fogging, which although moderately effective, will also affect beneficial insects such as pollinators (honey bees and butterflies) or affect other insects that are vital food sources for animals throughout the food chain. Larviciding is the introduction of insecticides into the water bodies that mosquitoes lay eggs which hatch as larvae, which although moderately effective, will contaminate water sources for other animals and affect organism in the water impacting the aquatic food chain. However, recently developed larvicides and insecticides have achieved much greater specificity in eliminating the targeted species with little or no effect on non-targeted insects. These methods are unfortunately labour intensive and the costs are inhibitive in large scale programmes where mosquito control is needed the most.

However, new methods are constantly being attempted to improve control strategies and these include the use of genetically modified mosquitoes and the use of motorized carbon dioxide fans to attract and trap mosquitoes.

Thus, there is a need for alternative means for preventing mosquitos biting hosts thereby preventing disease transmission.

There have been some suggestions, particularly in Chinese publications, that light may be modified to reduce insect attraction, WO2017/085682, for example, teaches filtering out wavelengths which act as attractants, and identifies, for example, the wavelengths 510-530 nm within a 6500K LED and 2700 k LED for hemiptera. Other wavelengths acting as attractants for various insects are identified in FIG. 4 and include wavelengths in the UV, blue and green regions of the 30 light spectrum.

CN20184931 teaches a 1 to 10 W LED with an anti-mosquito optical wavelength between 410-412 nm that may be used as a small night time lamp.

CN205155721 discloses a LED mosquito repellent window lamp with a coating for filtering out wavelengths other than 530-590 nm, which light is projected as a light curtain.

CN205155606 discloses a warm lamp with a colour temperature of 2700-4000K of 10 W power sending out 1000 lumens of light between 540 and 590 nm.

CN102937271 discloses a 1000 to 15000 K colour temperature LED mosqueto repelling LED lamp comprising a white light LED bead, a white light LED chip (comprising 5 a blue-light chip sprayed with a fluorescent powder) and a yellow light LED lamp bead and chip.

WO2016/068368 discloses a light emitting unit for preventing the approach of harmful insects and utilises phosphor to focus the wavelength to 500 to 550 nm.

JP2012243744 discloses a LED system for glass houses in which the LED light source with an indium gallium nitride type LED chip emitting light is modified to reduce the wavelength range 460-540 nm such that the light intensity is below half of that in the range 580-750 nm.

CN20204065 discloses a mosquito repellent candle.

It is clear from the above that the general approach is inconsistent and generally involves filtering of "attractant" wavelengths adding cost and complexity.

In contrast Applicant uses a combination of light intensity, colour temperature and broad spectra to repel mosquitos, particularly those from two spp which are

SUMMARY

In accordance with the present invention there is provided a method of repelling mosquitos from a locality or proximity (10; 22) where humans or animals will be present and/or inhibiting the mosquito from seeking a blood meal, comprising positioning lighting (18) at a location (12; 16) and in an orientation that will generate a photo-taxis repellent response and/or inhibit blood seeking by the mosquito, such that they are discouraged from entering a defined zone (22) which the lighting (18) protects and/or have a reduced tendency to seek a blood meal within the zone (10; 22) wherein the lighting is LED lighting and generates an intense light of at least 100 lux, with a colour temperature of greater than 5000K and has a cool white spectra with two peaks, a first peak at about 450 nm-470 nm and a second peak at about 500 nm-700 nm.

Preferably the method targets *Aedes* spp, particularly *Aedes aegypti* or *Aedes albopictus*.

More preferably the lighting emits an intense light over 200 lux. The optimal intensity appears to be in the region of 270 lux to 310 lux, optimally about 290 lux. More preferable the lighting emits light with a colour temperature in the range 5000K-10,000K.

According to a further aspect of the invention there is provided an LED or LED array which has been adapted to provide bespoke intensity, colour temperature and spectra for use to repel flying insects, particularly mosquitos.

The LED may accordingly be tuneable and/or may further comprise filters and/or amplifiers to remove or amplify given wavelengths to promote specificity for the required purpose. The LED may also take the form of a chip on board (COB) device.

To implement the method the lighting can be positioned in a manner that repels the mosquitos from entering a protected illuminated zone. For example, a LED light strip (or other arrangement) may be fitted to transmit light substantially across a door or window opening, substantially across a tent or awning opening, or around an outdoor seating area. In such scenario they may be positioned to create a curtain of light from the sides and or from above and/or below.

They may also be fitted to, for example, the underside or perimeter of a table, a marquee, awning or other articles or structures e.g. buildings, walls, posts etc. that will facilitate the controlled lighting of a zone or area for the intended purpose.

In a further embodiment one or more portable LED containing lanterns may be used in the method of the invention. The lantern may direct light in a uni-directional, bi-directional or multi-directional manner.

Where animals rather than humans are being protected the lighting may be positioned around animal housing, such as barns, stables and the like or dairy's where animals such as cows are brought for a specific purpose, particularly around dawn and dusk or at the optimal biting times of the target mosquito. The lighting should completely illuminate the animals to provide effective repellence.

The method of the invention may be used as a method of disease prevention, to control, for example, vector borne disease, such as, Dengue, Dengue Haemorrhagic Fever, Chikungunya, Mayaro, Usutu and Zika.

BRIEF DESCRIPTION OF THE DRAWINGS

Examples demonstrating various aspects of the invention are further described hereinafter with reference to the accompanying drawings, in which.

DETAILED DESCRIPTION

Based on a chance observation, Applicant undertook a series of Experiments to determine whether, contrary to the traditional approach of using light of given wavelengths to attract insects, mosquitos might in fact be repelled by light under certain conditions, and/or their tendency to take on a blood meal might be inhibited.

Experiment 1

In a first series of Experiments Applicant looked at whether the light intensity of LED's affected mosquito behaviour. To this end they looked at an array of 52 LED's (480 lux)—noted as 100% output, and reduced the output to 75% of the start output (39 LED's), 50% of the start output (26 LED's), 33% of the start output (17 LED's) and 10% of the start output (5 LED's) respectively. A separate control used no LED's.

The 5 LED array which still showed an effect (though clearly less than optimal) had a lux of about 75, and separate field trials indicate effects at as low as 10 lux may be effective.

The objective was to determine if the light at various intensities repelled the mosquitos-measured as Repellent Population rate RPr, and also whether it inhibited biting, based on the behavioural measure that landing in close proximity to a lure (carbon dioxide) equates to blood feed behaviour—measured as Repellent Landing rate RLr.

Repellent Population Rate (RPr):

RPr is a measure of the repellent effect of LEDS on mosquitoes based on the total number of mosquitoes released into a test chamber. This is a measure of repellence against a given population.

Thus, the higher the percentage, the greater the repellence effect.

$$\left( \frac{\text{Number of mosquitoes released} - \text{Number of mosquitoes caught at } rWith \text{ LED}'}{\text{Total number of mosquitoes released}} \right) \times 100\%$$

Repellent Landing Rate (RLr):

RLr is a measure of the repellent landing effect of LEDs on mosquitoes based on the total number of mosquito landings in a choice test environment.

Mosquito landings were assumed to be linked to the attempt by mosquitoes to take a blood meal; hence by recording the total number of landings, the potential number of blood meals can be estimated.

Thus, the higher the percentage, the greater the inhibition to take a blood meal.

$$\left( \frac{\text{Number of mosquitoes caught} - \text{Number of mosquitoes caught at } rWith \text{ LED}'}{\text{Total number of mosquitoes caught}} \right) \times 100\%$$

Figure 4:
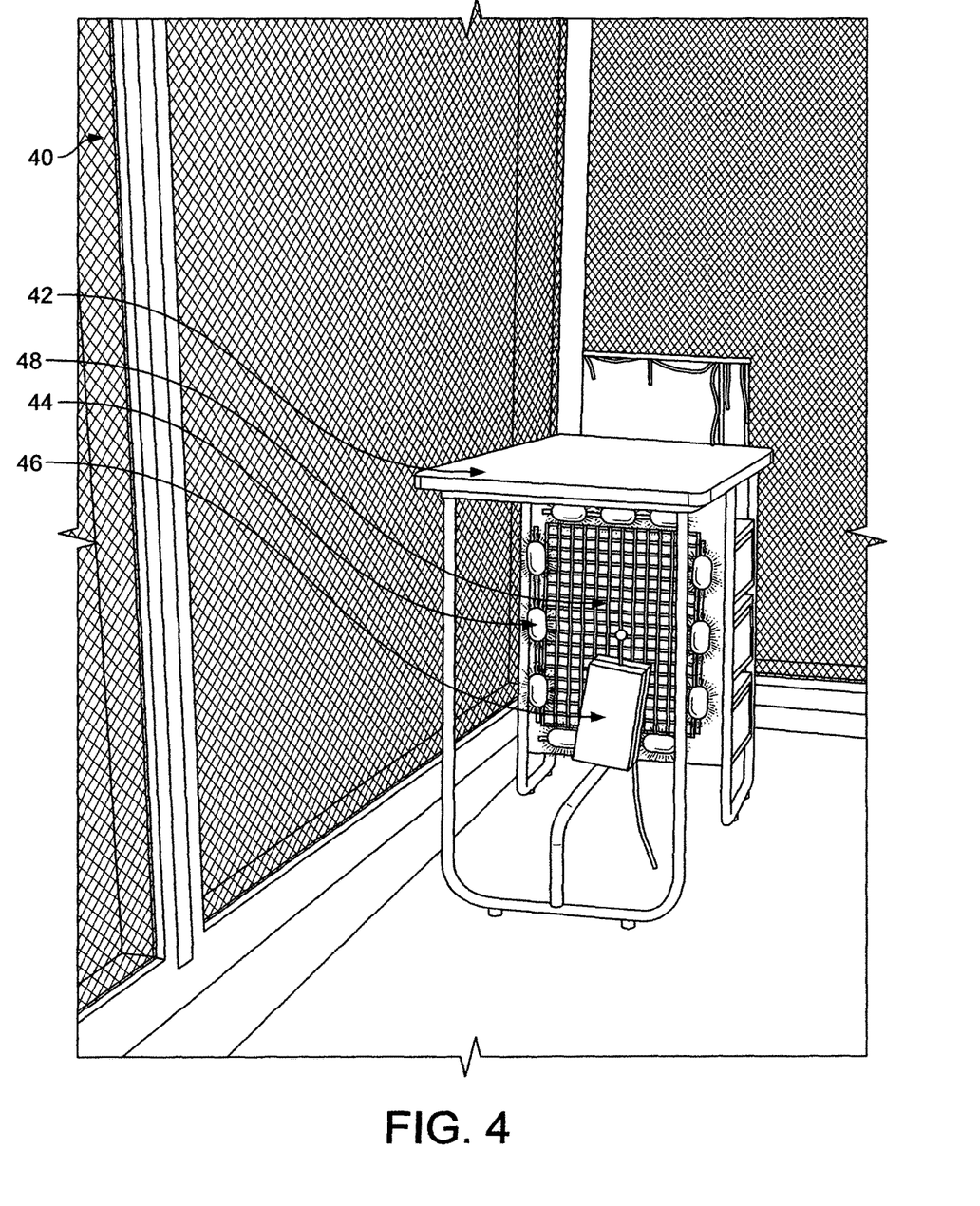
FIG. 4 is a representation of the test environment used in Experimental series 1, in which various LED intensities were tested in a variety of orientations (combined data results shown)

The experiments were run in a cage (40) (approx. size 5 m×5 m×4 m) as illustrated in FIG. 4 in which a desk (42) had fitted to it a lighting source (44), shown 5 projecting light in a sideway orientation with an associated lure (46) (carbon dioxide release) and capture means (48) a glueboard. Alternative light projections—up, and down were also tested.

A number (250) of *Aedes* spp mosquitoes or *Culex* spp mosquitoes were released into the cage (40) and the effect of light (44) was monitored over time (2 hours).

The results of various experiments are provided below.

Experiment 1.1 Cumulative Results.

Figure 6A:
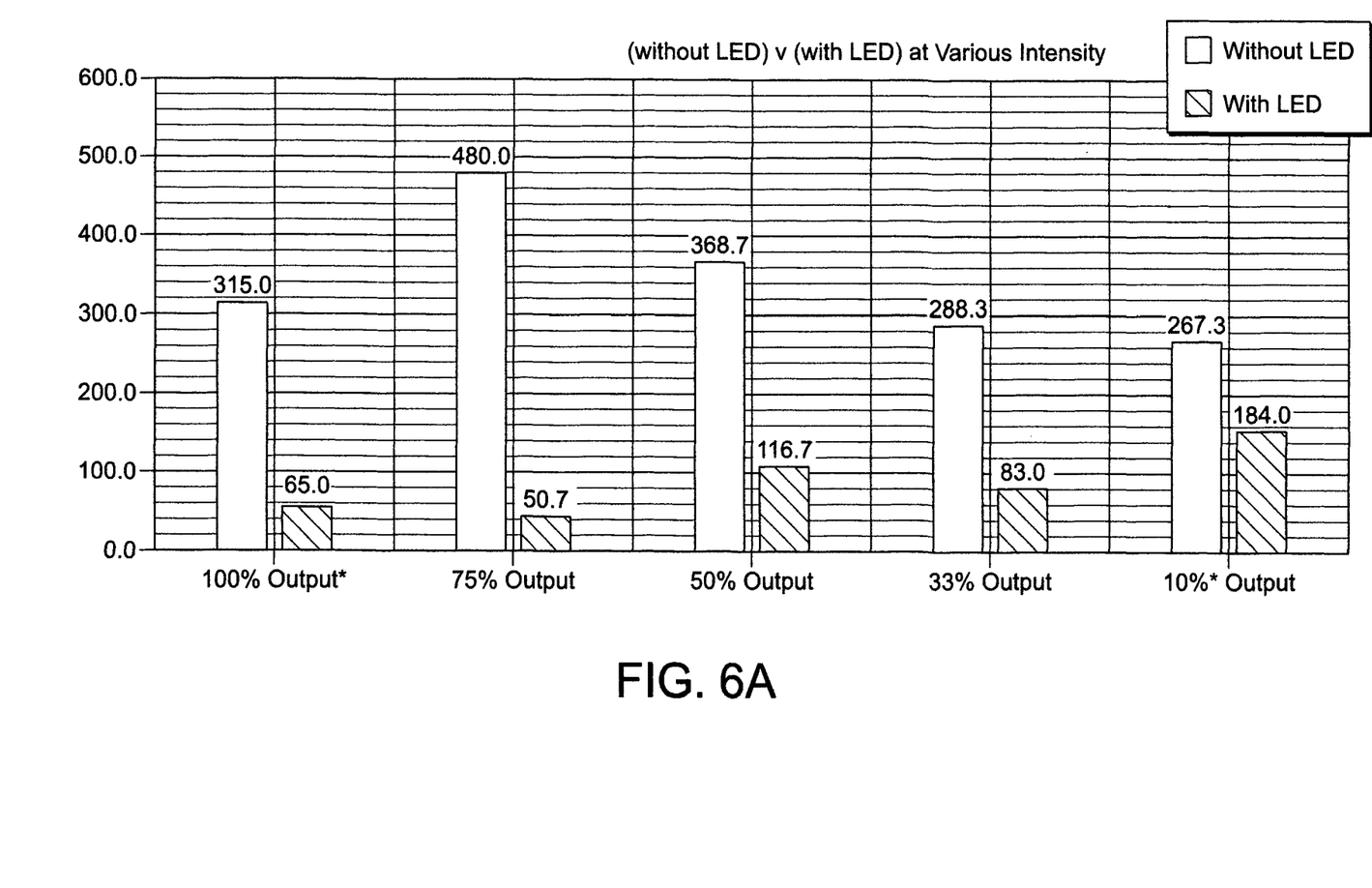
FIG. 6A is graphically presented data, generated from Experimental series 1, comparing average catch rates without light with light of varying intensities: 100%=52 LED's (480 Lux), 75%=39 LED's, 50%=26 LED's, 33%=17 LED's and 10%=5 LED's.

FIG. 6A shows the cumulative results. As will be seen from the catch figures, the highest intensity (52 LED's) gave a repellence of 79%, with the highest effect 89% seen with 39 LED's. As the intensity reduced the repellence reduced such that at 10% (5 LED's) the repellence was only 31%.

The effect was however highly statistically significant with a t test between the 75% output (with LED and without) providing a p value of 0.003.

Experiment 1.2 and 1.3

Figure 6B:
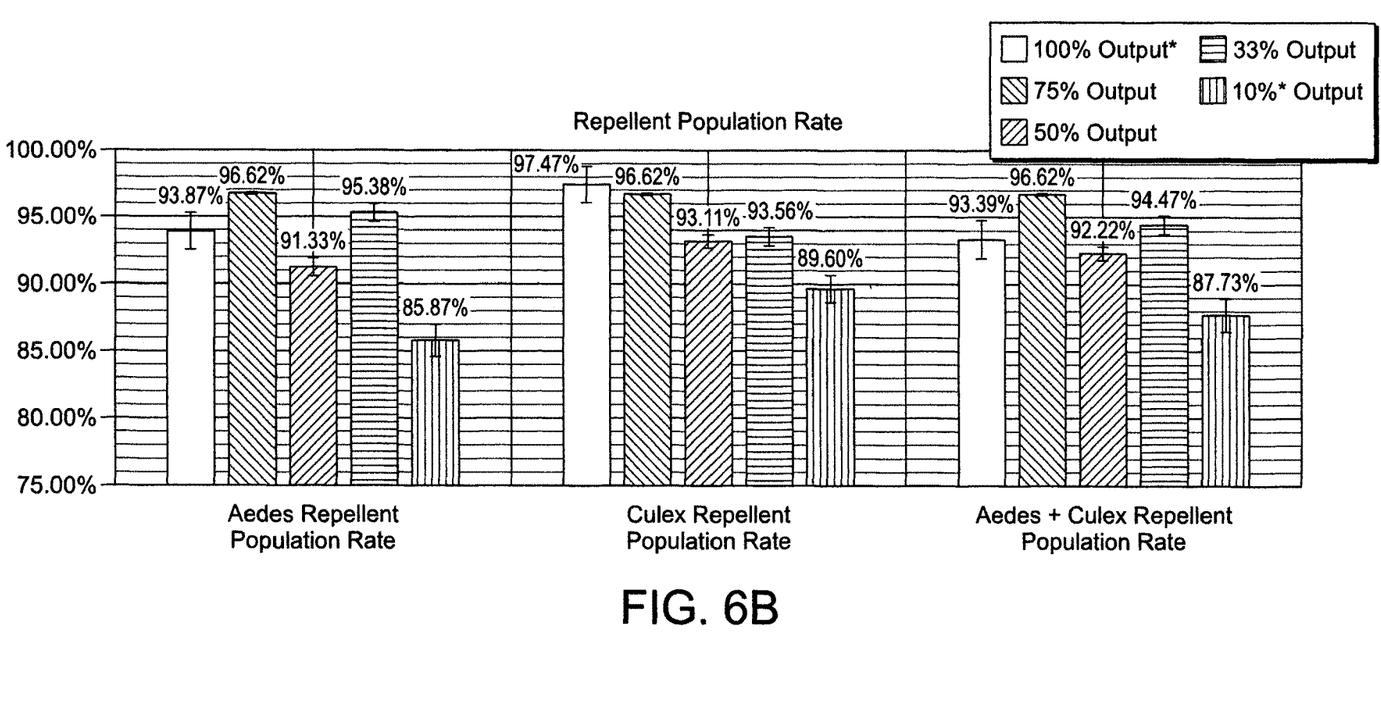
FIG. 6B is graphically presented data generated from Experimental series 1 comparing the Repellent Population rate (a negative photo taxis response) on two different mosquito species: left hand side—*aedes*, middle—*Culex*, and right hand side combined data.
Figure 6C:
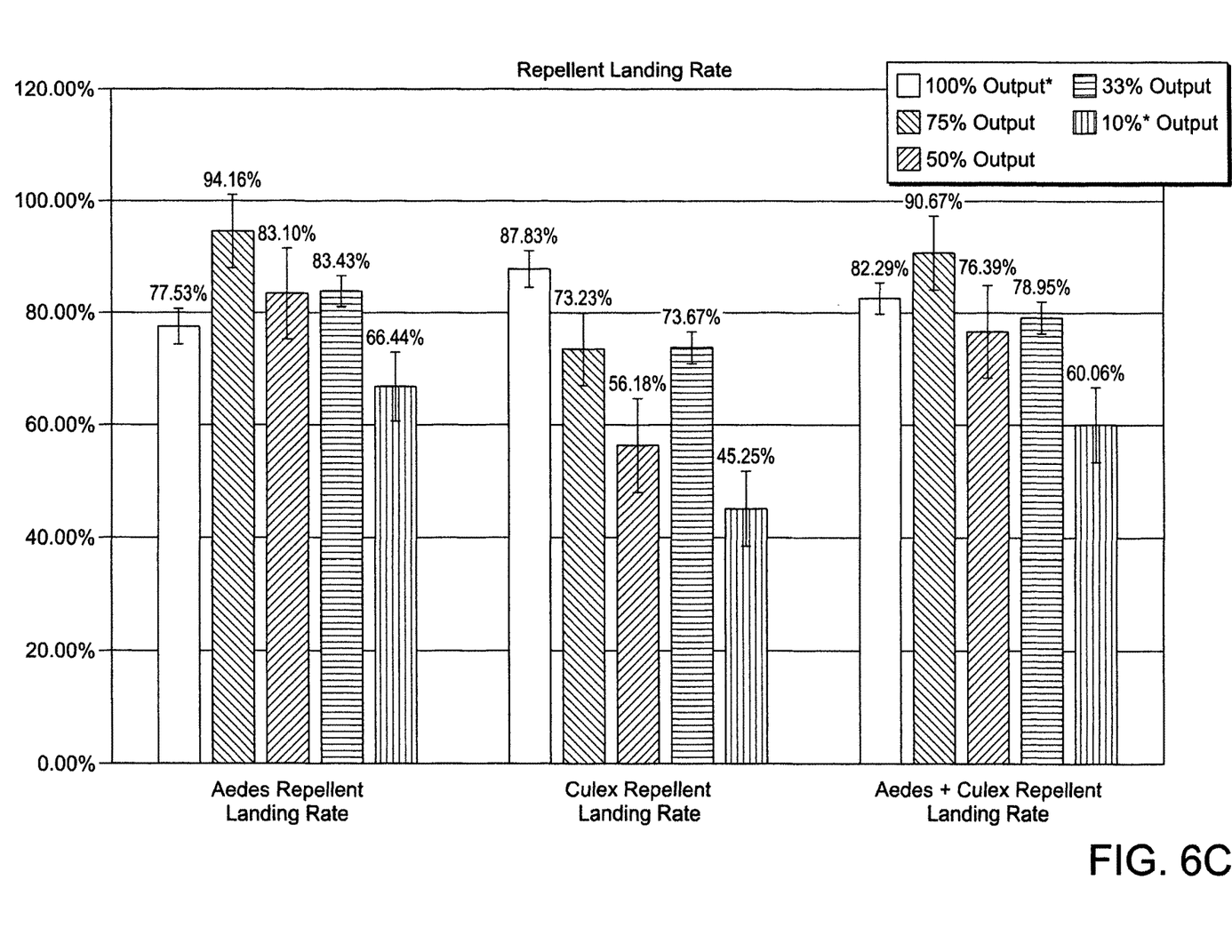
FIG. 6C is graphically presented data generated from Experimental series 1 comparing the Repellent Landing rate (behaviour equating to taking a blood meal) on two different mosquito species: left hand side—*Aedes*, middle—*Culex*, and right hand side 20 combined data.
Figure 7A:
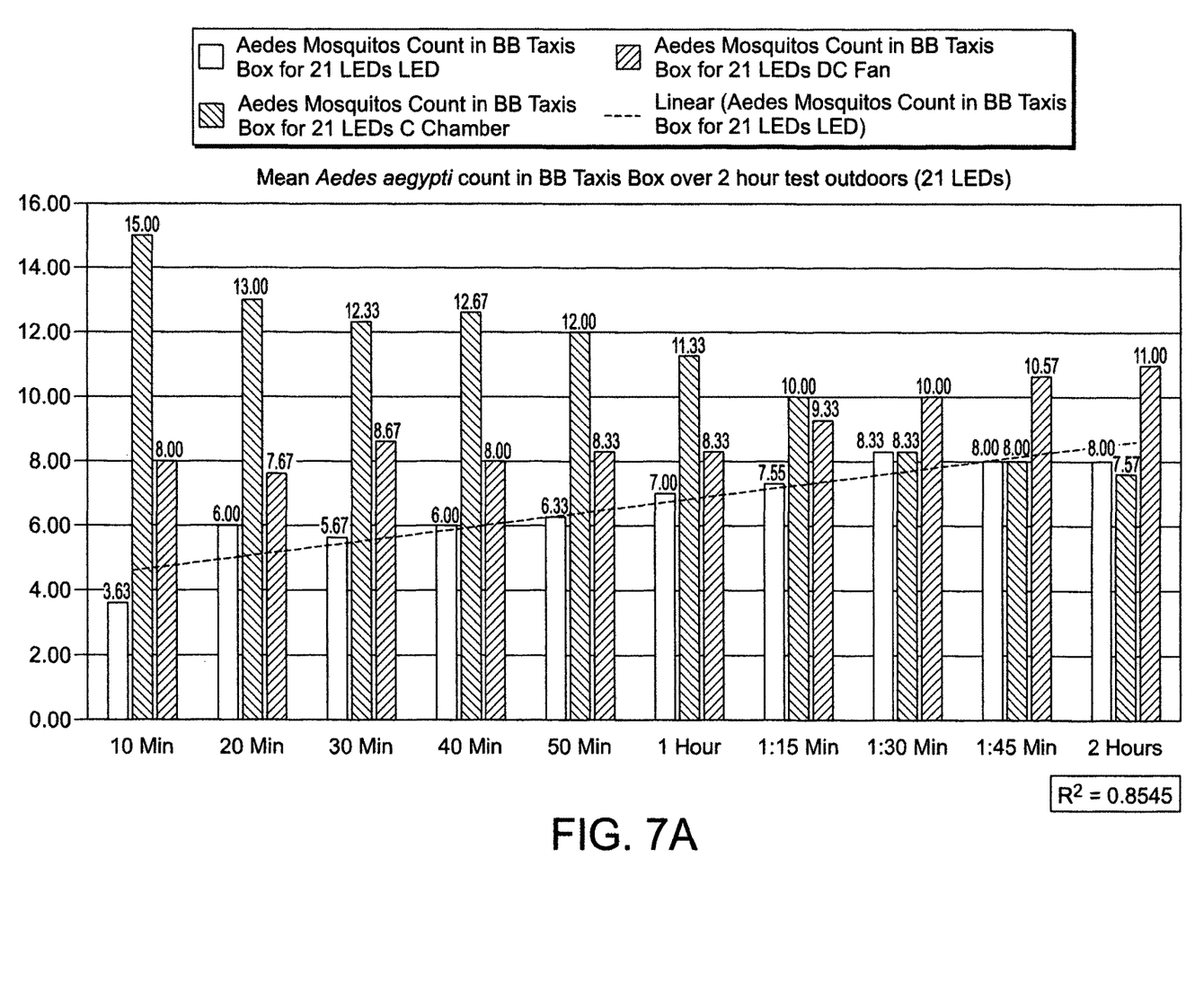
FIG. 7A is graphically presented data generated from Experimental series 2 comparing the movement of *Aedes* mosquitos in a choice test chamber over a 2 hour period with 21 LED's (227 lux)
Figure 7B:
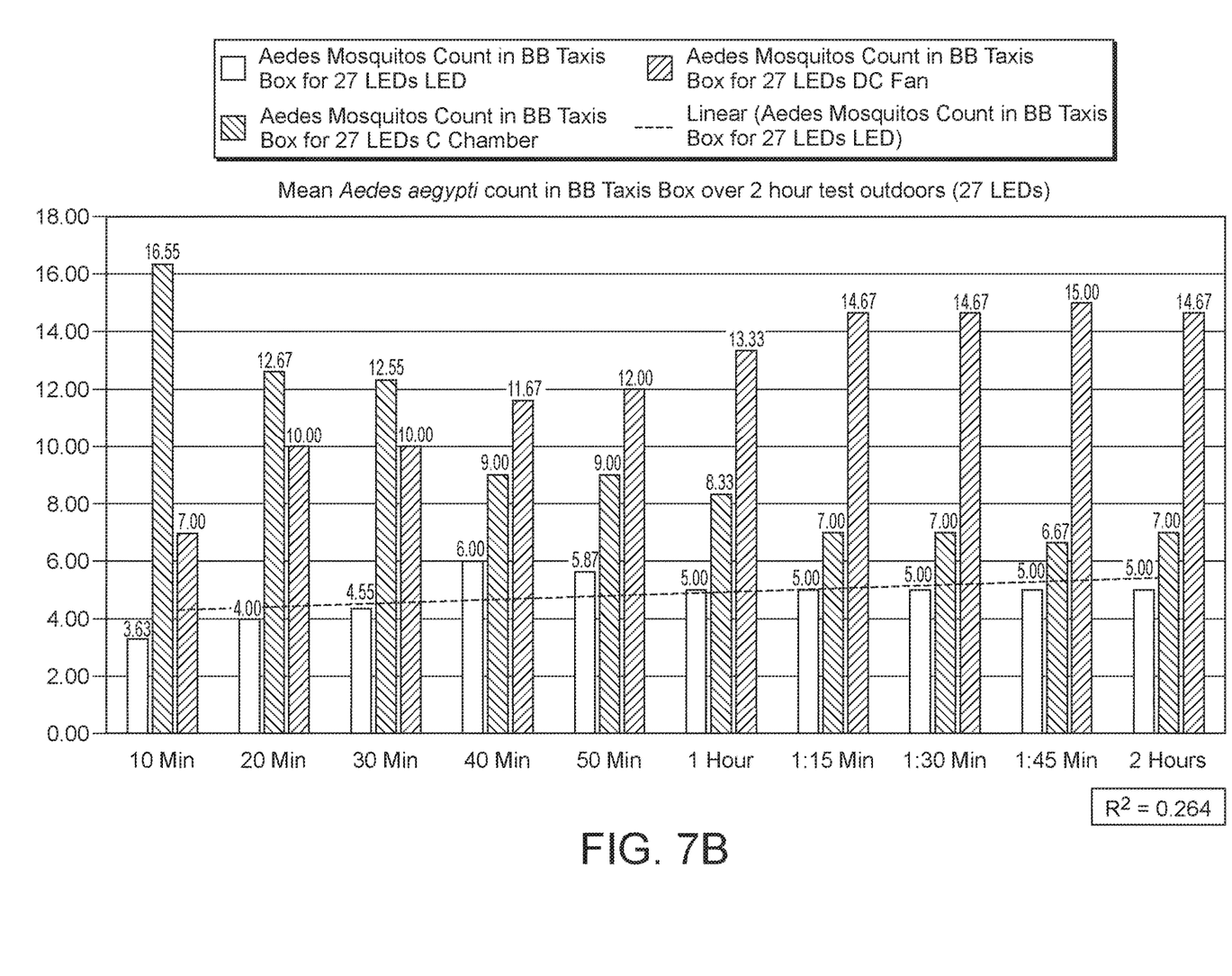
FIG. 7B is graphically presented data generated from Experimental series 2 25 comparing the movement of *Aedes* mosquitos in a choice test chamber over a 2 hour period with 27 LED's (267 lux)
Figure 7C:
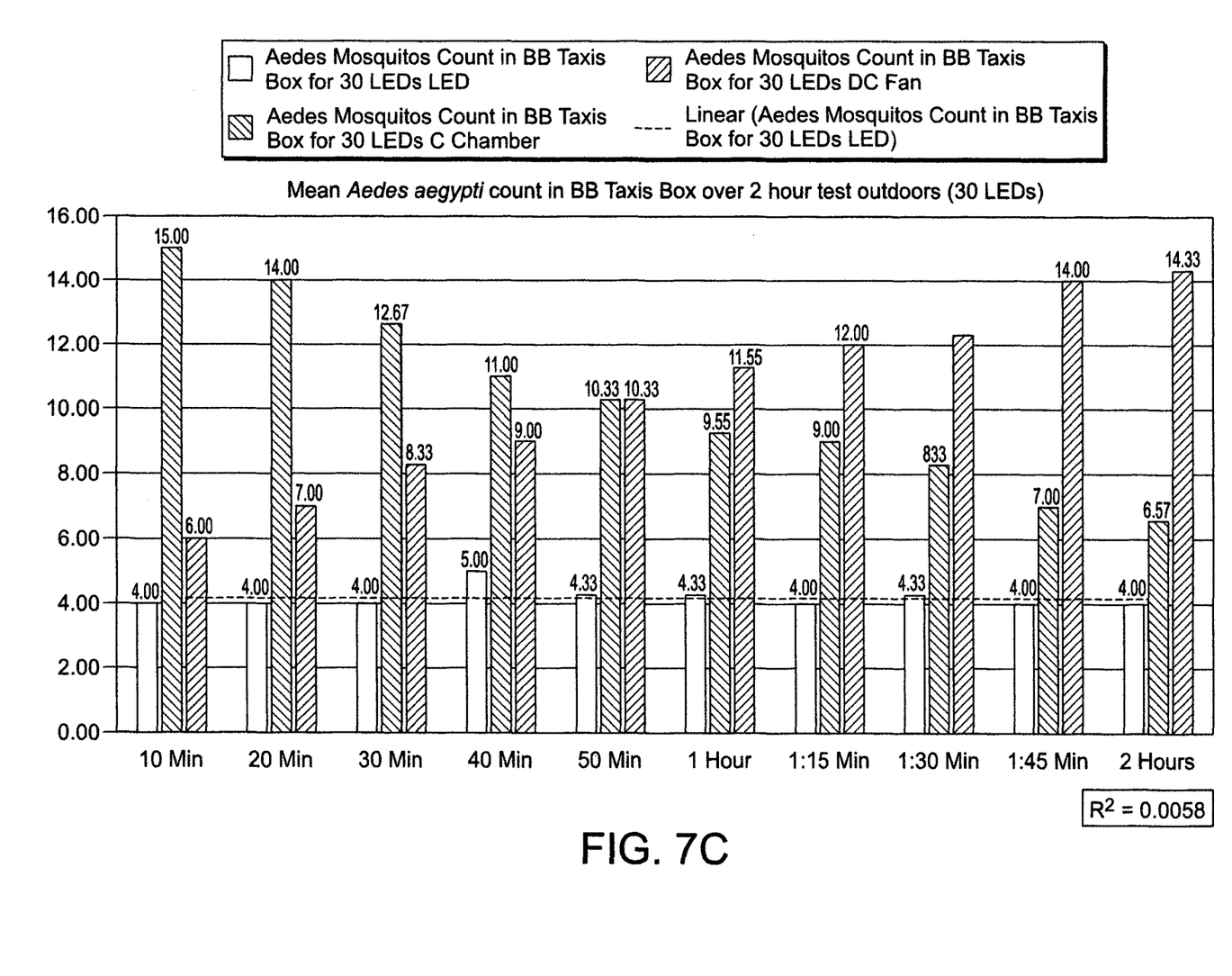
FIG. 7C is graphically presented data generated from Experimental series 2 comparing the movement of *Aedes* mosquitos in a choice test chamber over a 2 hour period with 30 LED's (293 lux)
Figure 7D:
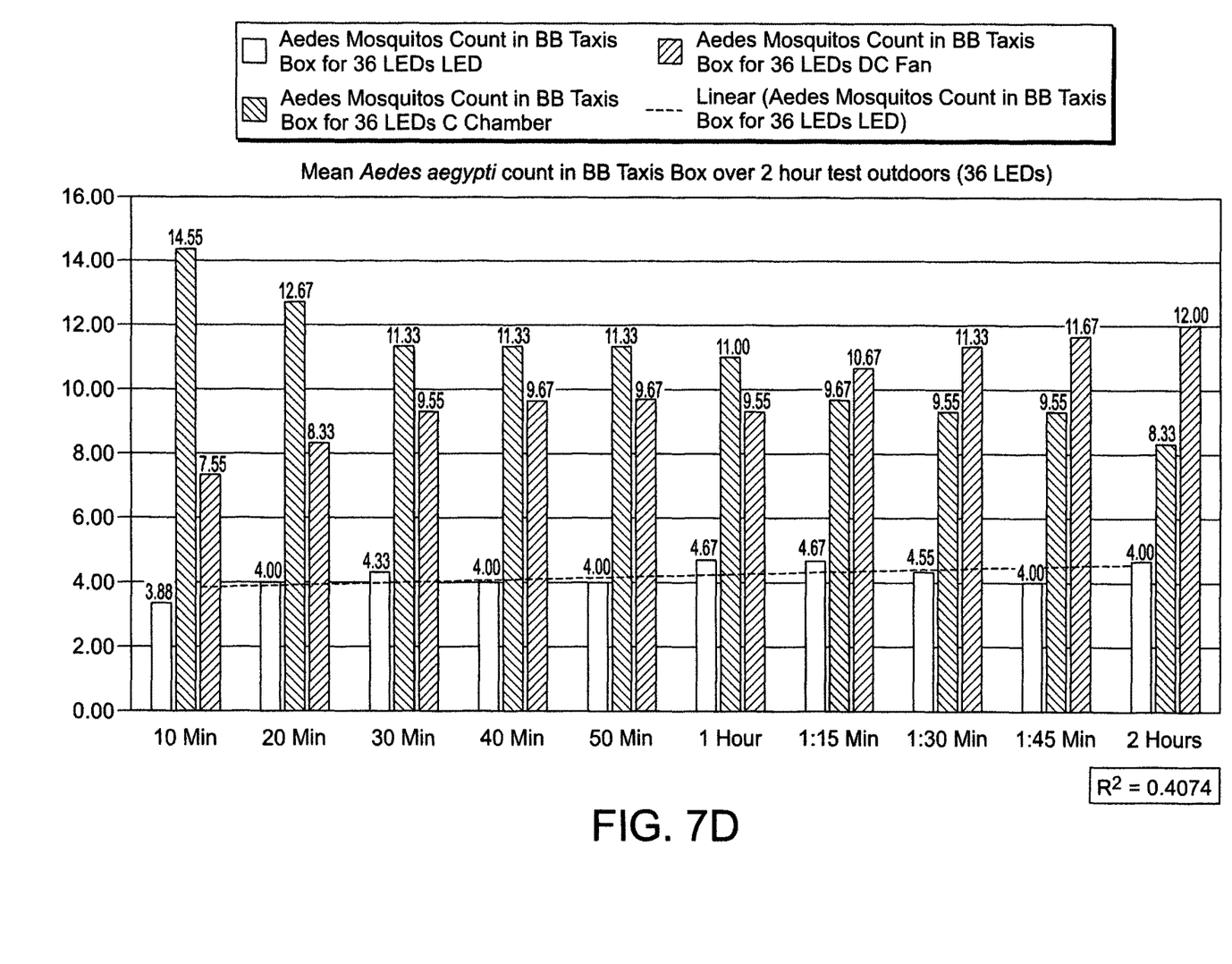
FIG. 7D is graphically presented data generated from Experimental series 2 comparing the movement of *Aedes* mosquitos in a choice test chamber over a 2 hour period with 36 LED's (347 Lux).

FIG. 6B and FIG. 6C show respectively the effect on RPr, and RLr. In general the RPr for the higher intensity LED configurations was over 90% and the PLr for the higher intensity LED configurations was over 75%. The results were highly statistically significant and demonstrate the dual benefits of the approach.

Experiment 2

Using the knowledge gained from Experiment 1 (including direction of lighting—up/down/sideways—all effective) Applicant built an apparatus (50) (FIG. 5) comprising five compartments (from left to right)—A, B, C, D and E. Compartment A contains an end cap opening (52) with a wire mesh (54) and is separated from the rest of the chamber by mesh netting. This is the chamber into which a lure (56) (warm blooded mammal) is placed. Compartment E, at the opposite end is equivalent but has an exhaust fan and battery (58) associated therewith instead of a lure, and draws air through the apparatus as indicated by the arrows. Adjacent compartments A and E are compartments B and D which function as "choice chambers" with compartment C positioned between compartments B and D, and which serves as the "release chamber" into which mosquitos are introduced before being released by opening gates (60). Once acclimatised the mosquitos are free to move between the chambers and in the normal course of events (no lights) fly towards chamber A containing the lure.

Figure 2:
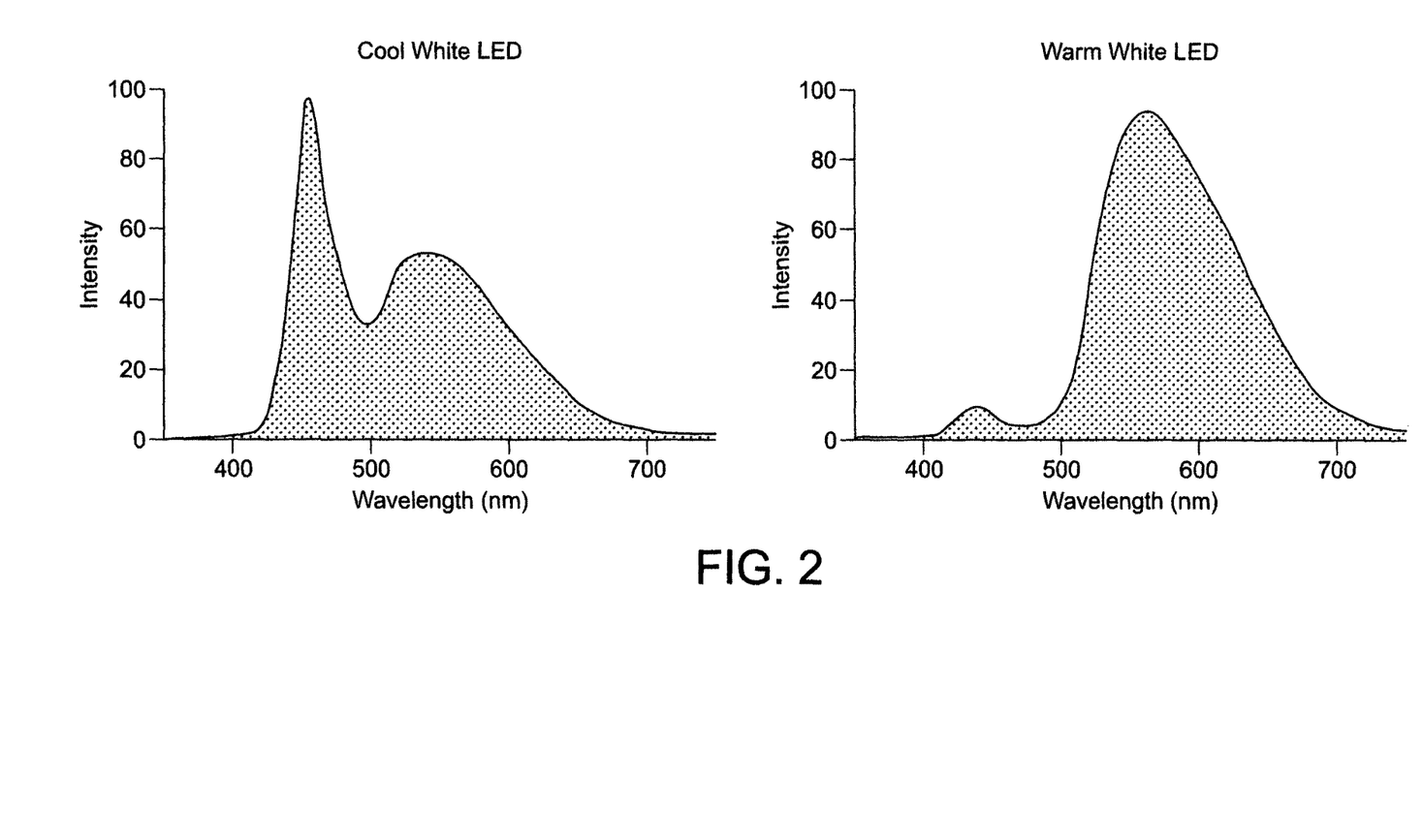
FIG. 2 is a diagram illustrating the different wavelength profiles between a cool white light LED (left) and a warm white light LED (right)
Figure 3:
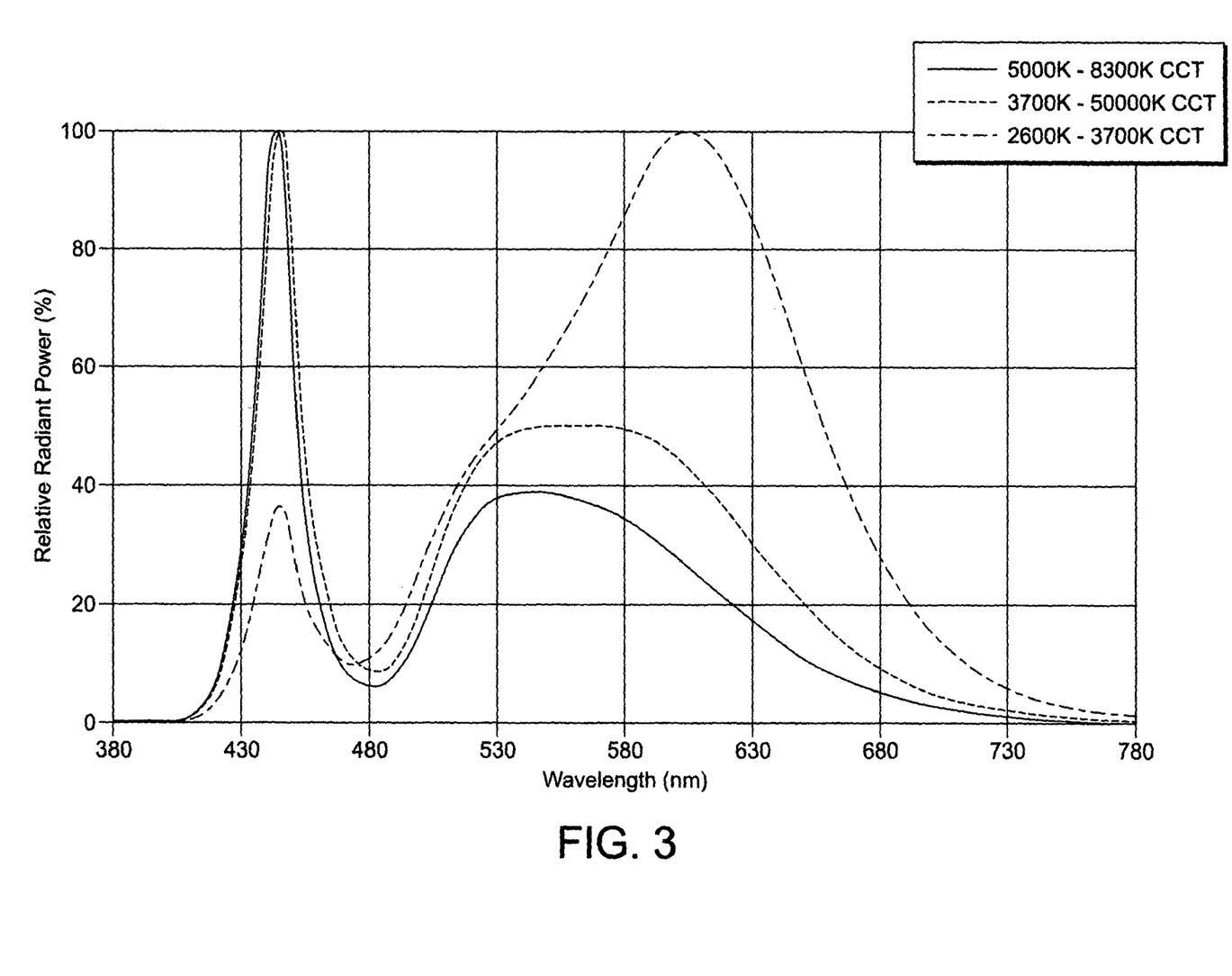
FIG. 3 is a diagram showing the different colour temperature profiles—the LEDs used in the invention fell into the 5000K plus range.

When lights, such as are described herein, are placed in Compartment B, and operated under different conditions: e.g. intensity, measured by lux, colour temperature, measured by Kelvin (see FIG. 3), spectra, measured by nanometre (See FIG. 2), and orientation e.g. a curtain (up/down/ and/or side illumination, direction towards or away from the approaching mosquito the behaviour of the mosquito could be evaluated and the Experiments conducted and selective results obtained are provided in FIGS. 7 A-7D below:

Methodology

A modified Taxis box was used to assess the repellent nature of LEDs to host seeking unfed *Aedes* spp mosquitoes.

25 female *Aedes* spp mosquitoes were placed in Compartment C and allowed to acclimatize.

Figure 5:
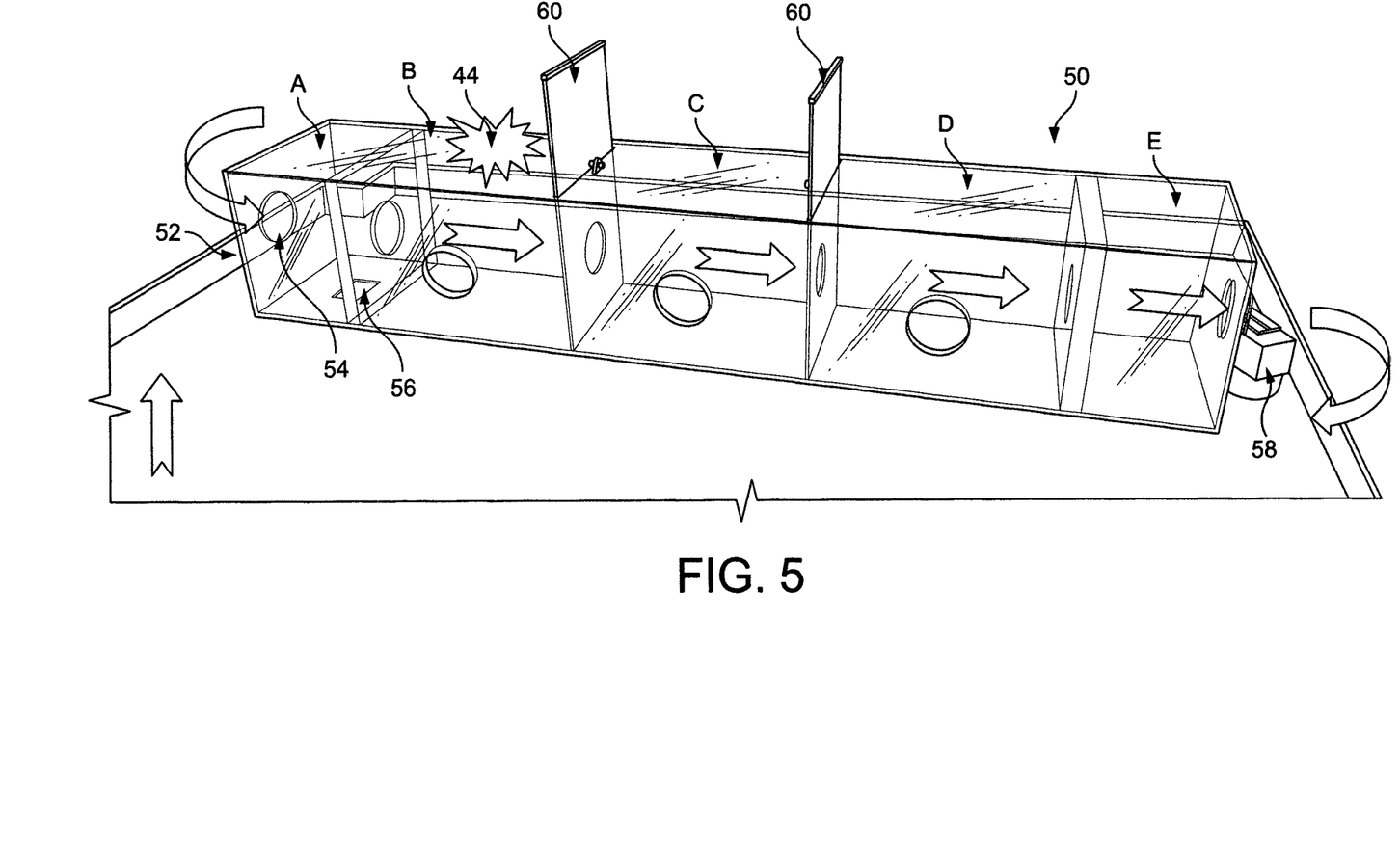
FIG. 5 is a representation of an apparatus used in Experimental series 2, in which specific intensities (lux) were studies under more controlled conditions.

The fan (58) was connected at the DC fan location and set to the 'exhaust' position to draw air through the Taxis box.

A live immobilized rodent (56) was placed outside the LED box allowing air to be drawn over the rodent and fill the Taxis box with the scent of a blood meal creating a scent gradient the mosquitoes can utilize.

Various LED strips/arrays (44) were tested with varying intensity (lux), with a known number of LEDs placed as close as possible to the immobilized rodent (56) and LEDs variously orientated with respect to the flight path of the mosquitoes.

The fan (58) is switched on and the gates (60) trapping the mosquitoes in Chamber C are opened to allow the host seeking mosquitoes to travel upwind through the scent gradient created by the immobilized rodent.

The number of mosquitoes in each chamber are counted at timed intervals for 2 hours and recorded and analysed for differences.

Results

From the results obtained and illustrated with reference to FIGS. 7A-7D it will be apparent that light intensity plays a significant role in repellence, and that 21 LED's giving a lux of 227 (FIG. 7A) do not provide a level of repellence that would be considered sufficiently effective.

In contrast, with 27 LED's—giving a lux of 267 (FIG. 7B), one starts to see a clear trend of mosquitos favouring compartment D ($3^{rd}$ grey column) to compartment B ($1^{st}$ blue column) with time. i.e. they move away from the light (44) despite the presence of the lure (56).

With 30 LED's, 293 lux (FIG. 7C), there is a very strong repellent trend with over 80% of the mosquitos moving away from the light (44) throughout a 2 hour period.

This trend remains strong with 36 LED's (347 lux) (FIG. 7D), although it appears that increasing the lux beyond a given point does not result in further improvement, and indeed the lux of about 300 appears optimum.

As well as the lux, it would appear that the type of LED's selected also play a significant role in facilitating the repellent responses. Indeed, the selection of "cool white" LED's (FIG. 2 left hand side), as opposed to warm white light (FIG. 2 right hand side) is significant. The "cool white" light has a very different signature to that of "warm white" light, as will be apparent from both FIGS. 2 and 3. Indeed, the colour temperature of greater than 5000K (FIG. 3) with a high amplitude first peak between about 450 nm and 470 nm, and a lower amplitude, and broader, second peak between about 500 nm and 700 nm has also been demonstrated to be significant.

Figure 1:
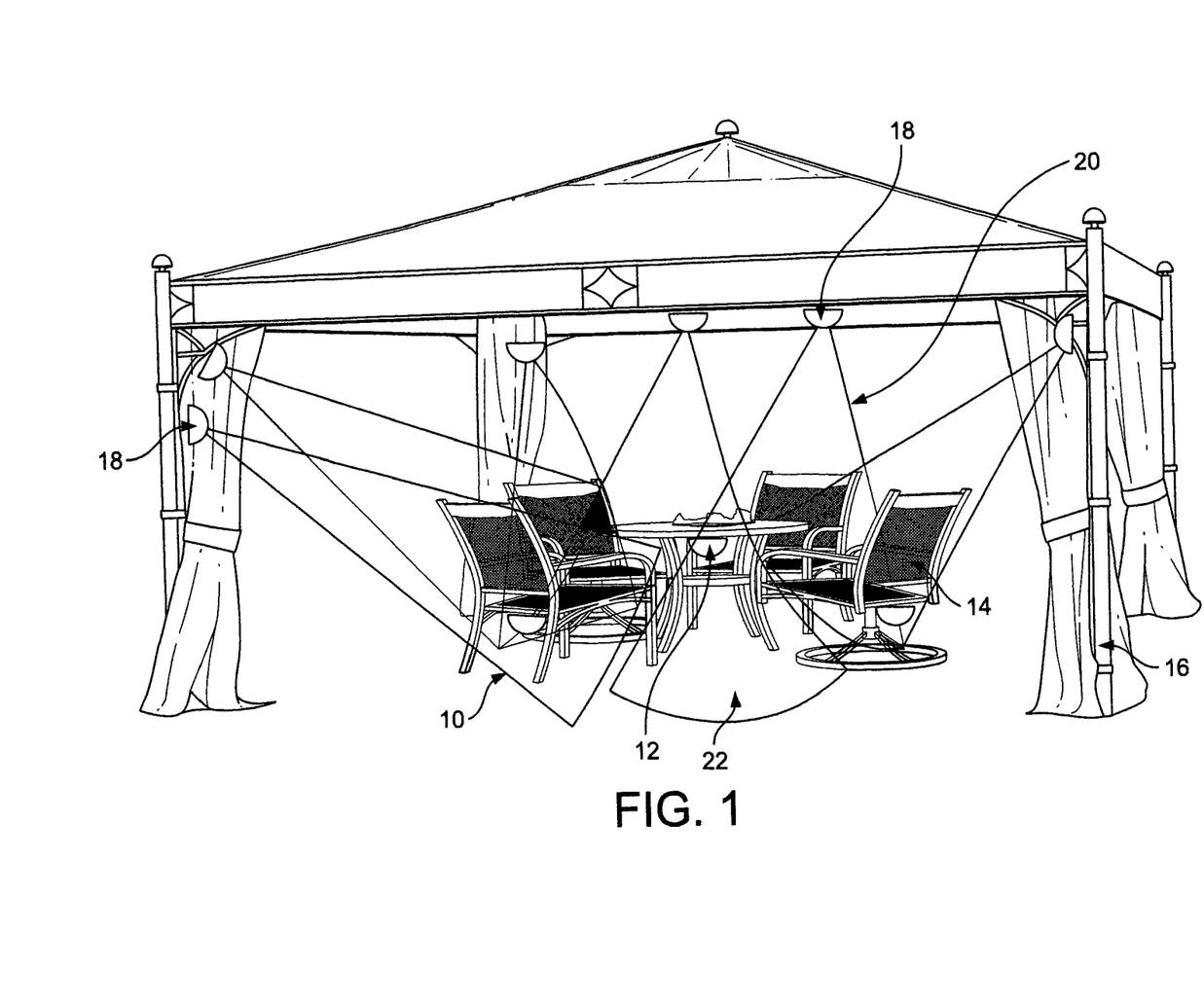
FIG. 1 is a representation of lighting being used as a mosquito repellent in a seating area.

The findings facilitate the applications of bespoke lighting solutions in the management of mosquitos a, for example, illustrated by FIG. 1 which shows a seating area (10) comprising a table (12) and chairs (14) under a gazebo (16) on which are mounted lights (18) which are angled and positioned to project light (20) into the area (10) to illuminate a zone (22), which illuminated zone serves to repel mosquitos.

The skilled person will understand from the above that there are many other examples which lend themselves to protection using the teaching of the invention.

The invention claimed is:

1. A method of repelling mosquitos from a locality or proximity where humans or animals will be present and/or inhibiting the mosquito from seeking a blood meal, comprising: positioning lighting at a location and in an orientation that will at least one of generate a photo-taxis repellent response and inhibit blood seeking by the mosquito, such that the mosquito at least one of (i) is discouraged from entering a defined zone which the lighting protects, and (ii) has a reduced tendency to seek a blood meal within the zone; wherein the lighting is LED lighting and generates an intense light of at least 100 lux, with a colour temperature of greater than 5000K and has a cool white spectra with two peaks, a first major peak at about 450 nm-470 nm and a second lesser peak at about 500 nm-700 nm2 wherein the first major peak transitions to the second lesser peak at about 480 nm; wherein wavelengths of about 470 nm to 490 nm of the intense light have a relative radiant power of less than 20%; wherein the first major peak has a relative radiant power of about 100%; and wherein the second lesser peak has a relative radiant power of less than 40%.

2. A method as claimed in claim 1, wherein the mosquitos targeted are at least one of *Aedes* spp, *Aedes aegypti*, and *Aedes albopictus*.

3. A method as claimed in claim 1, wherein the intense light generates at least 200 lux.

4. A method as claimed in claim 3, wherein the intense light generates between 270 and 310 lux.

5. A method as claimed in claim 4, wherein the intense light generates about 290 lux.

6. A method as claimed in claim 1, wherein the lighting emits light with a colour temperature in a range 5000K-10000K.

7. A method as claimed in claim 1, comprising fitting an LED light strip to transmit light across a door or window opening.

8. A method as claimed in claim 1, comprising fitting an LED light strip to transmit light across a tent or awning opening.

9. A method as claimed in claim 1, comprising fitting an LED light strip around an outdoor seating area.

10. A method as claimed in claim 1, comprising fitting an LED light strip to at least one of an underside of a table and a perimeter of the table.

11. A method as claimed in claim 1, comprising using one or more portable LED containing lanterns.

12. A method as claimed in claim 1, wherein the method is for disease prevention.

13. The method as claimed in claim 1, wherein: the intense light is an unfiltered intense light; and at least one of (i) the photo-taxis repellent response in the mosquito is generated with the unfiltered intense light and (ii) the mosquito is inhibited from blood seeking with the unfiltered intense light.

14. A method of repelling at least one mosquito from an area, the method comprising: positioning an LED lighting at a location and in an orientation relative to a desired zone; generating an intense unfiltered light of at least 100 lux via the LED lighting, the intense unfiltered light having (i) a colour temperature greater than 5000K and (iii) a cool white spectra with two peaks, the two peaks including a first major peak at about 450 nm-470 nm and a second lesser peak at about 500 nm-700 nm; protecting the zone via at least one of (i) generating a photo-taxis repellent response in the at least one mosquito with the intense unfiltered light and (ii) inhibiting blood seeking by the at least one mosquito with the intense unfiltered light; wherein protecting the zone includes at least one of (i) discouraging the at least one mosquito from entering the zone and (ii) reducing a tendency of the at least one mosquito to seek a blood meal within the zone; wherein the first major peak transitions to the second lesser peak at about 480 nm; wherein wavelengths of about 470 nm to 490 nm of the intense light have a relative radiant power of less than 20%; wherein the first major peak has a relative radiant power of about 100%; and wherein the second lesser peak has a relative radiant power of less than 40%.

15. A method of repelling at least one mosquito from an area, the method comprising: positioning an LED lighting at a location and in an orientation relative to a desired zone; generating an intense light of 270 lux to 310 lux via the LED lighting, the intense light having (i) a colour temperature greater than 5000K and (iii) a cool white spectra with two peaks, the two peaks including a first major peak at about 450 nm-470 nm and a second lesser peak at about 500 nm-700 nm; protecting the zone via at least one of (i) generating a photo-taxis repellent response in the at least one mosquito with the intense light and (ii) inhibiting blood seeking by the at least one mosquito with the intense light; wherein protecting the zone includes at least one of (i) discouraging the at least one mosquito from entering the zone and (ii) reducing a tendency of the at least one mosquito to seek a blood meal within the zone; wherein the first major peak transitions to the second lesser peak at about 480 nm; wherein wavelengths of about 470 nm to 490 nm of the intense light have a relative radiant power of less than 20%; wherein the first major peak has a relative radiant power of about 100%; and wherein the second lesser peak has a relative radiant power of less than 40%.

* * * * *